United States Patent [19]

Brehm

[11] Patent Number: 4,739,753
[45] Date of Patent: Apr. 26, 1988

[54] SURGICAL DRAPE SUPPORT AND OXYGEN DELIVERY SYSTEM

[75] Inventor: Erich G. Brehm, Garland, Tex.

[73] Assignee: Brehm, Inc., Duncanville, Tex.

[21] Appl. No.: 89,677

[22] Filed: Aug. 26, 1987

[51] Int. Cl.[4] .......................................... A61M 16/00
[52] U.S. Cl. ........................... 128/200.24; 128/204.18; 128/205.26; 128/132 D
[58] Field of Search ............... 128/202.13, 202.16, 128/202.18, 204.18, 204.25, 205.26, 139, 132 D, 132 R, 200.24; 604/281, 282

[56] References Cited

U.S. PATENT DOCUMENTS

| | | | |
|---|---|---|---|
| 1,060,665 | 5/1913 | Bell | 604/281 |
| 2,999,497 | 9/1961 | Hamilton et al. | 128/204.18 |
| 3,169,528 | 2/1965 | Knox, III et al. | 604/281 |
| 3,403,677 | 10/1968 | Struve | 128/132 D |
| 3,859,993 | 1/1975 | Bitner | 128/205.26 |
| 4,205,668 | 6/1980 | Criddle | 128/132 D |
| 4,321,917 | 3/1982 | Campbell | 128/204.18 |
| 4,363,323 | 12/1982 | Geiss | 604/281 |
| 4,377,161 | 3/1983 | Whitt | 128/204.18 |
| 4,498,473 | 2/1985 | Gereg | 604/282 |

FOREIGN PATENT DOCUMENTS 0180348  5/1986  European Pat. Off. ............ 604/282

*Primary Examiner*—Kyle L. Howell
*Assistant Examiner*—Timothy G. Philips
*Attorney, Agent, or Firm*—Richards, Harris, Medlock & Andrews

[57] ABSTRACT

An air delivery system (10) for supplying air from a source (28) includes a flexible conduit (20). Structure (22, 24) is provided for connecting the conduit (20) to the air supply (28). A nozzle (44) is attached to the conduit (20) and is adjustable and positionable through placement of the flexible conduit (20), such that air is delivered to the face (16) of a patient (12) without the nozzle (44) or the flexible conduit (20) contacting the patient (12). The system (10) also supports a drape (14) above the face (16) of the patient (12).

1 Claim, 1 Drawing Sheet

SURGICAL DRAPE SUPPORT AND OXYGEN DELIVERY SYSTEM

TECHNICAL FIELD

This invention relates to surgical instruments, and more particularly to a system for delivering oxygen, air or anesthetic gases to a patient during a surgical procedure as well as for supporting a drape over the patient.

BACKGROUND OF THE INVENTION

During surgical procedures, such as for example, cataract operations, it is necessary to supply oxygen to the patient. Typically, a cannula is inserted into the nasal passageway to provide the necessary oxygen to the patient. A nasal cannula is generally uncomfortable for the patient and may result in irritation to the nasal passages.

During surgical procedures, it is also often required to cover the patient's body with a surgical drape, such that only the body portion undergoing surgery is exposed. In cataract surgery, for example, the patient's face is draped leaving the eye undergoing surgery exposed. Frequently, patients feel claustrophobic due to the drape covering his or her face. The surgical drape may also be annoying to the patient since the drape comes in contact with the patient's face.

A need has thus arisen for a system that can deliver oxygen or air to a patient in the area of the patient's face without the need for a cannula, but which adequately provides a source of oxygen to the patient during a surgical procedure. A need has also arisen for a drape support system which maintains the drape off a patient's face to reduce claustrophobic feelings and irritation which can lead to patient movement which interferes with the surgical procedure.

SUMMARY OF THE INVENTION

In accordance with the present invention, an air delivery system for supplying air, oxygen or anesthetic gases from a source to a patient includes a flexible conduit having first and second ends. Structure is provided for connecting the conduit first end to the air source. A nozzle is attached to the conduit second end and is adjustable and positionable through placement of the flexible conduit such that the nozzle is supported above the face of a patient and air is directed to the face of the patient without the nozzle or the flexible conduit contacting the patient. The conduit also serves to support a surgical drape above the face of the patient.

BRIEF DESCRIPTION OF THE DRAWINGS

For a more complete understanding of the present invention and for further advantages thereof, reference is now made to the following Detailed Description taken in conjunction with the accompanying Drawings in which.

DETAILED DESCRIPTION

Figure 1:
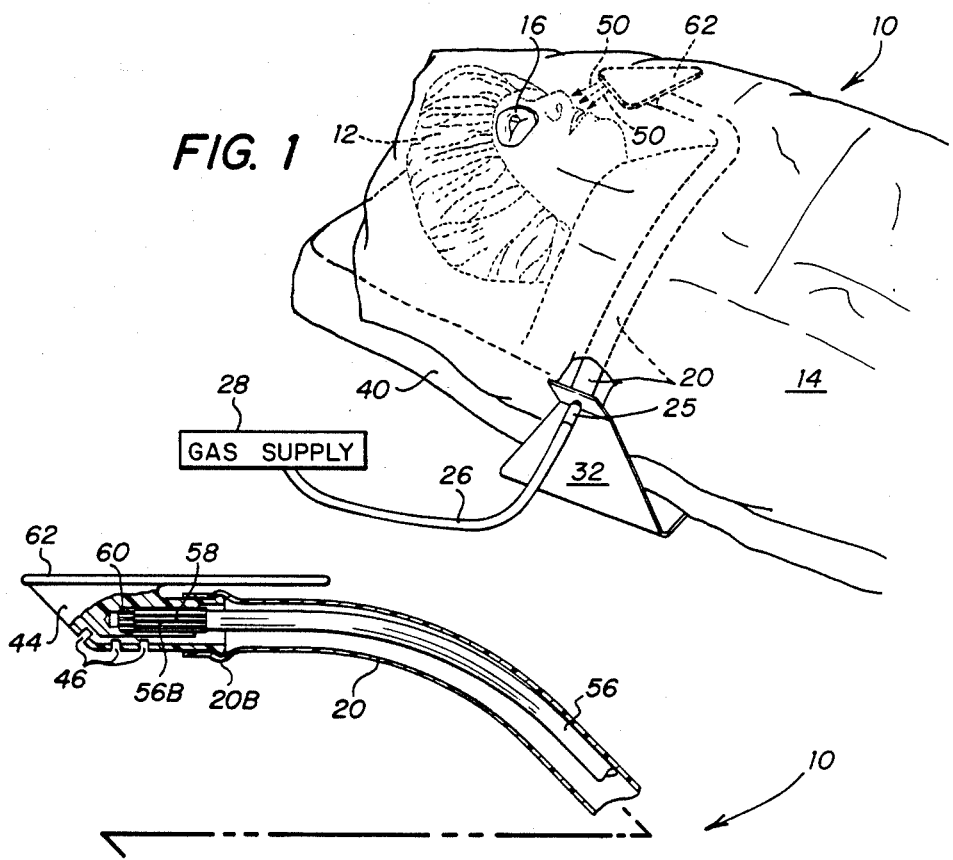
FIG. 1 is a pictorial illustration of a patient utilizing the present surgical drape support and oxygen delivery system.
Figure 2:
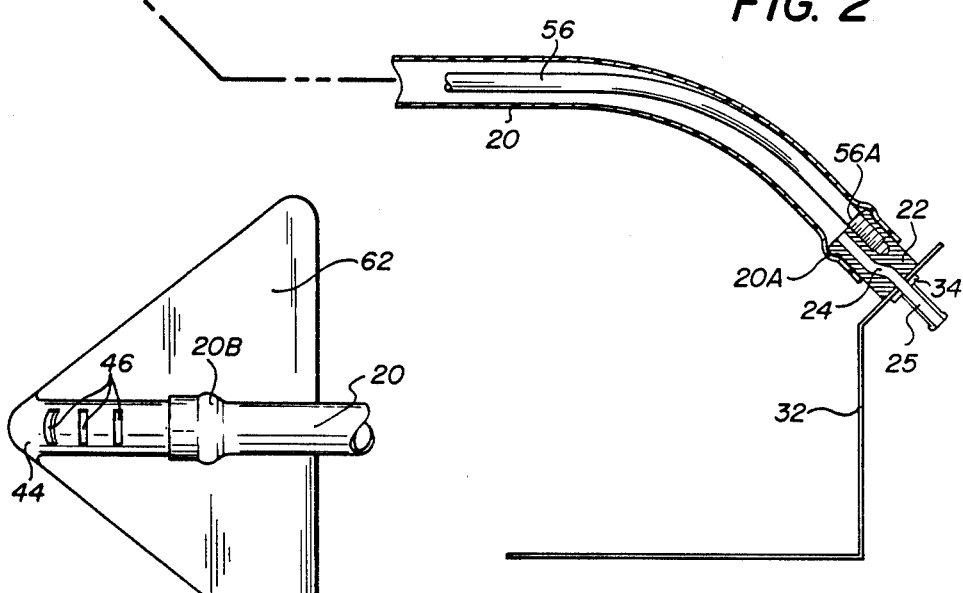
FIG. 2 is a side elevational view, partially in section, of the system illustrated in FIG. 1.
Figure 3:
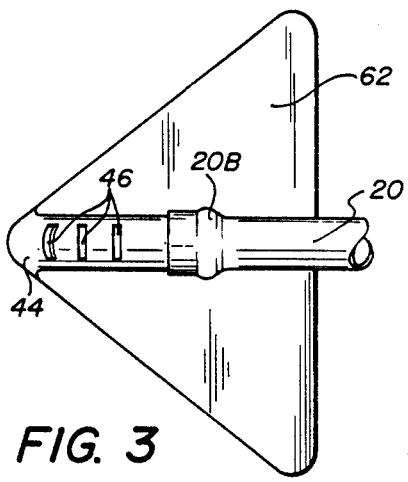
FIG. 3 is a bottom plan view of the nozzle and tray of the present invention.

Referring simultaneously to FIGS. 1, 2 and 3, the present surgical drape support and oxygen delivery system of the present invention is illustrated and is generally identified by the numeral 10. System 10 is utilized for delivering oxygen, air, anesthetic gases or a combination thereof, hereinafter referred to as air, to the area of a patient's face without the use of a cannula during a surgical procedure. The present system also supports a surgical drape above the face of the patient to thereby reduce the claustrophobic feeling a patient may feel during the surgical procedure. Although, FIG. 1 illustrates a patient 12 having an eye exposed from beneath a surgical drape 14, the eye being prepared for cataract surgery, the present system 10 can be utilized for numerous types of surgical procedures, and FIG. 1 is shown for illustrative purposes only. System 10 is positioned under drape 14 as illustrated in FIG. 1, and thereby supports drape 14 above the face 16 of patient 12.

As more clearly illustrated in FIG. 2, system 10 includes a flexible conduit 20 having ends 20a and 20b. Flexible conduit 20 may be fabricated from any type of copper, plastic or rubber tubing, and may have a diameter of, for example, ⅜ inches. End 20a of flexible conduit 20 is interconnected to a socket 22 through which extends an aperture 24. Aperture 24 is aligned with a tube 25 which receives a supply conduit 26 (FIG. 1) which is interconnected to a gas supply 28. Gas supply 28 may comprise, for example, a tank supplied oxygen source, anesthetic gas source, a wall mounted supply source and various pumps to selectively control a flow rate of air being delivered to patient 12. Socket 22 is supported on a bracket 32. Socket 22 may be interconnected to bracket 32 such as by welding, gluing or a mechanical fastener 34 which is also received by tube 25. Bracket 32 is positioned under a mattress 40 supported on an operating room table or by other clamping devices supported on an operating room table or surgical stretcher.

Air is supplied to flexible conduit 20 from gas supply 28 via supply conduit 26 through tube 25 to the interior of flexible conduit 20. Attached to end 20b of flexible conduit 20 is a nozzle 44 having apertures 46 through which air passes to the face 16 of patient 12. FIG. 1 diagrammatically illustrates the flow of air illustrated by arrows 50 from nozzle 44 to face 16 of patient 12. Therefore it can be seen that air from gas supply 28 is routed through flexible conduit 20 to the face 16 of patient 12. Flexible conduit 20 can be positioned along the body of patient 12 and is positionable adjacent face 16 of patient 12 as desired and can assume numerous configurations.

Disposed within flexible conduit 20 is a flexible rod 56. Rod 56 is threadedly received in socket 22 at end 56a. End 56b of rod 56 includes splines 58 which mate with grooves 60 within nozzle 44. Nozzle 44 is positioned by aligning splines 58 and grooves 60. Rod 56 may comprise, for example, copper and provides support for flexible conduit 20. Rod 56 is capable of bending to numerous configurations and provides a degree of rigidity for flexible conduit 20 to allow flexible conduit 20 to support surgical drape 14 above face 16 of patient 12. Surgical drape 14 is supported along the entire length of flexible conduit 20 between ends 20a and 20b.

Integrally formed with nozzle 44 is a tray 62. Tray 62 is supported by nozzle 44 which, in turn, is supported by flexible rod 56. In use, tray 62 is disposed under surgical drape 14 and provides a surface for holding surgical instruments and other material utilized during surgery.

Therefore it can be seen that the present surgical drape support and oxygen delivery system provides for the delivery of oxygen from an air supply source to the area around the face of a patient without the use of nasal cannulas. The present system also comfortably supports a surgical drape above the face of a patient to reduce claustrophobic feelings of a patient during surgery.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An apparatus for supporting a surgical drape and supplying breathing gas from a source having a supply line to a patient, comprising:

a support bracket;

a socket attached to said support bracket, said socket having an aperture extending therethrough from a first side to a second side;

a tube attached to said first side of said socket and aligned with said aperture, said tube extending from said support bracket and adapted for receiving the gas supply line from the source of breathing gas;

a flexible conduit having a first end attached to said second side of said socket, said flexible conduit receiving breathing gas from the supply line through said tube and said aperture;

a flexible rod having a first end connected to said second side of said socket and extending inside said flexible conduit for supporting said flexible conduit;

a nozzle attached to a second end of said flexible conduit and a second end of said flexible rod;

said nozzle having a pllurality of grooves;

said flexible rod including means for mating with said plurality of grooves for selectively, rotatably positioning said nozzle with respect to said flexible conduit;

said nozzle having a tray disposed thereon for supporting the surgical drape above the patient; and said nozzle being repeatably adjustable and selectively positionable by bending said flexible rod within said flexible conduit so that breathing gas is directed to the patient while said flexible rod maintains said nozzle, tray, and flexible conduit out of contact with the patient.

* * * * *